(12) United States Patent
Hoogerwerf

(10) Patent No.: US 9,079,003 B1
(45) Date of Patent: Jul. 14, 2015

(54) CREAM AND OINTMENT APPLICATOR

(71) Applicant: Leasa Kay Hoogerwerf, Menifee, CA (US)

(72) Inventor: Leasa Kay Hoogerwerf, Menifee, CA (US)

( * ) Notice: Subject to any disclaimer, the term of this patent is extended or adjusted under 35 U.S.C. 154(b) by 0 days.

(21) Appl. No.: 14/275,936

(22) Filed: May 13, 2014

Related U.S. Application Data

(60) Provisional application No. 61/832,803, filed on Jun. 8, 2013.

(51) Int. Cl.
*A46B 11/00* (2006.01)
*A61M 35/00* (2006.01)

(52) U.S. Cl.
CPC .......... *A61M 35/003* (2013.01); *A46B 11/0003* (2013.01); *A46B 11/0075* (2013.01)

(58) Field of Classification Search
CPC .... A46B 11/00; A46B 11/001; A46B 11/003; A46B 11/0075; A47K 7/02
USPC .................. 15/104.93, 104.94, 244.1–244.2; 401/132–135
See application file for complete search history.

(56) References Cited

U.S. PATENT DOCUMENTS

| | | | | |
|---|---|---|---|---|
| 3,485,562 A * | 12/1969 | Cairns et al. | ........ | 401/134 |
| 4,148,318 A * | 4/1979 | Meyer | ........ | 604/3 |
| 4,291,697 A * | 9/1981 | Georgevich | ........ | 604/3 |
| 4,299,005 A * | 11/1981 | Brown | ........ | 15/244.2 |
| 4,788,733 A * | 12/1988 | Lerner | ........ | 15/104.94 |
| 5,493,749 A * | 2/1996 | Zayas | ........ | 15/244.2 |
| D388,535 S | 12/1997 | Per-Lee | | |
| 5,692,261 A | 12/1997 | Lops | | |
| 5,823,206 A | 10/1998 | Mapleback | | |
| 5,842,488 A * | 12/1998 | Belleau et al. | ........ | 132/320 |
| 5,875,512 A * | 3/1999 | Lathan | ........ | 15/210.1 |
| 5,931,591 A | 8/1999 | McCracken | | |
| D448,521 S | 9/2001 | Angeletta | | |
| D487,164 S | 2/2004 | Denton | | |
| 6,981,293 B2 * | 1/2006 | Steinberg | ........ | 15/210.1 |
| D572,407 S | 7/2008 | Cook et al. | | |
| D587,844 S | 3/2009 | Slavin et al. | | |
| D636,934 S | 4/2011 | Chen | | |
| D679,806 S | 4/2013 | Davitt | | |
| 2001/0034920 A1 * | 11/2001 | Brown | ........ | 15/244.1 |
| 2007/0130706 A1 | 6/2007 | Buhrow et al. | | |
| 2008/0127994 A1 * | 6/2008 | Rippl et al. | ........ | 134/6 |
| 2010/0318041 A1 | 12/2010 | Cook | | |

* cited by examiner

*Primary Examiner* — Laura C Guidotti
(74) *Attorney, Agent, or Firm* — Loyal McKinley Hanson

(57) ABSTRACT

An applicator for the topical application of a rash-treating substance to a baby's bottom without transferring the substance to a caregiver's hands includes a handle component and a disposable sponge component adapted to be mounted removably on the handle component. A sponge portion of the sponge component includes a quantity of a rash-treating substance. In one embodiment, (a) the sponge portion is premoistened with a rash-treating substance and covered with a sponge-sealing cover that the caregiver removes prior to using the applicator, (b) the sponge component snaps removably onto the distal end portion of the handle component, (c) the distal end portion of the handle component pivots, and (d) the handle component includes a slide component that enables the caregiver to release the sponge component from the distal end portion of the handle component by sliding the slide component.

5 Claims, 3 Drawing Sheets

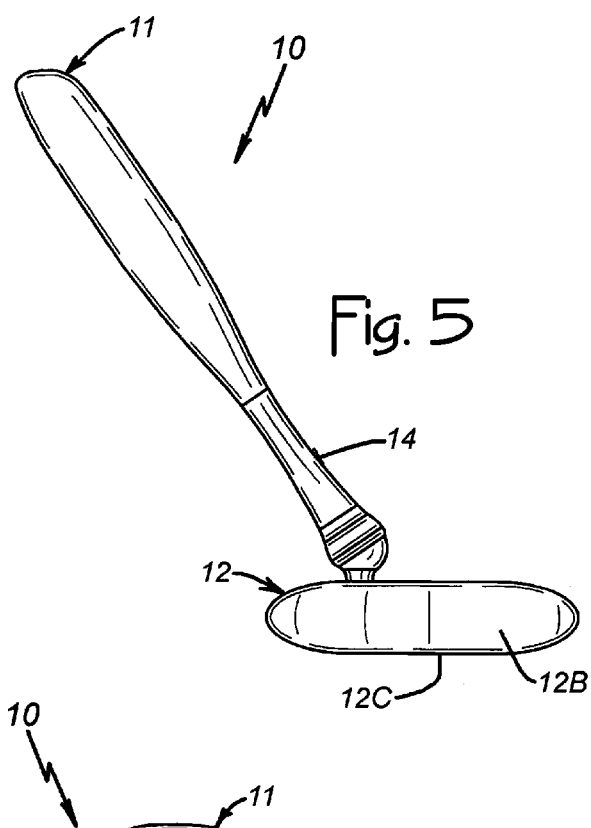
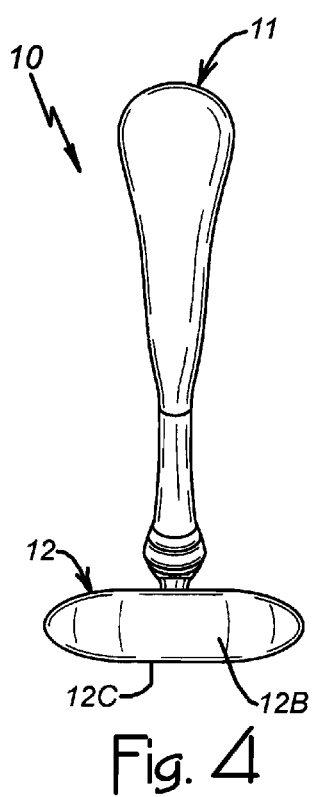
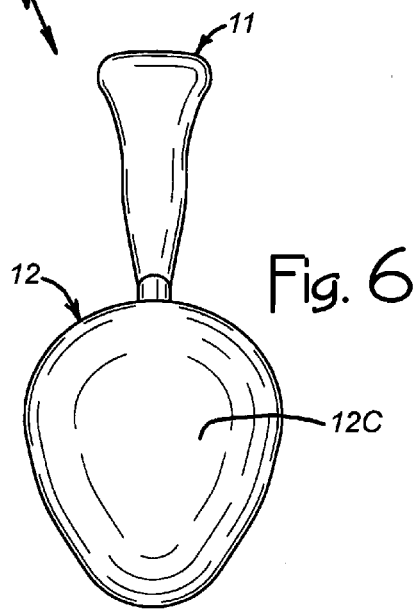
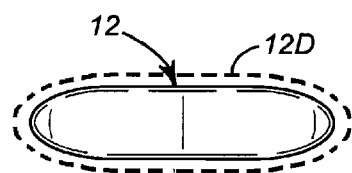

CREAM AND OINTMENT APPLICATOR

CROSS REFERENCE TO RELATED APPLICATION

This application claims the benefit of U.S. Provisional Patent Application Ser. No. 61/832,803 filed Jun. 8, 2013.

BACKGROUND OF THE INVENTION

1. Technical Field

This invention relates generally to the field of diaper rash and applicators for topical treatment of a baby's bottom with cream, ointment, and/or other rash-treating substances.

2. Description of Related Art

Diaper rash is a well known and commonly occurring form of inflamed skin (dermatitis) that appears as a patchwork of bright red skin on a baby's bottom (beneath the diaper). It is commonly linked to continuously wet or infrequently changed diapers, to diarrhea, and to using plastic pants to cover diapers. It also may develop after solid foods are added to the baby's diet, when breast-feeding mothers eat certain foods, or when the baby is taking antibiotics.

Simple home remedies are often all that is needed, including frequent diaper changes, extended periods of exposure to air, and other adjustments to diapering practices. In addition, the baby's parent or other caregiver often applies a cream, ointment, or other rash-treating substance by squeezing some onto the baby's bottom from a tube or other container of the substance, and then spreading it over the rash with their hand. One of the problems of doing so is that the substance transfers to the caregiver's hand(s) where it is unsightly, uncomfortable, and difficult to remove, even by washing. Thus, a need exists for a way to alleviate this concern.

SUMMARY OF THE INVENTION

In view of the foregoing, it is a primary object of the present invention to alleviate the concern outlined above. The present invention achieves this objective by providing an applicator having a wand (i.e., a handle component) that holds a tip or head (i.e., a disposable sponge component) such that the disposable sponge component includes a quantity of rash-treating substance. The caregiver holds the handle while applying the substance with the sponge, and thereafter manipulates a latch mechanism on the handle (e.g., a slide) to release the sponge component into the trash. Transfer of the substance to the caregiver's hands is avoided.

To paraphrase some of the more precise language appearing in the claims and further introduce the nomenclature used, an applicator constructed according to the invention includes a handle component and a sponge component. The handle component (e.g., about five inches long) has a proximal end portion, a distal end portion, and an intermediate portion extending between the proximal and distal end portions. The sponge component includes a sponge-holding portion and a sponge portion held by the sponge-holding portion. The sponge-holding portion is adapted to be mounted removably on the distal end portion of the handle component and the sponge portion includes a quantity of a rash-treating substance for the caregiver to apply to a baby's bottom.

In one applicator embodiment, the sponge portion is premoistened with a rash-treating substance and sealed in a sponge-sealing cover that the caregiver removes prior to using the applicator. In addition, (a) the sponge component snaps removably onto the distal end portion of the handle component, the (b) distal end portion of the handle component pivots, and (c) the handle component includes a slide component that enables the caregiver to release the sponge component from the distal end portion of the handle component by sliding the slide component.

Thus, the invention avoids transfer of the rash-treating substance to the caregiver's hand(s). The following detailed description and accompanying illustrative drawings make the foregoing and other objects, features, and advantages of the invention more apparent.

BRIEF DESCRIPTION OF THE DRAWINGS

FIG. 4 is a back elevation view;

FIG. 5 is a right side elevation view;

FIG. 6 is a bottom view;

FIG. 7 is a side elevation view of just the sponge component with the sponge-sealing cover shown diagrammatically as a circumscribing broken line.

DESCRIPTION OF THE PREFERRED EMBODIMENTS

Figure 1:
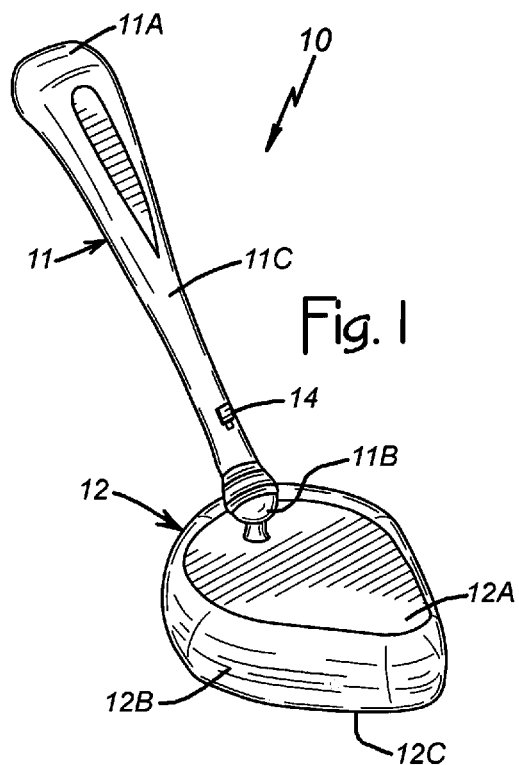
FIG. 1 of the drawings is a perspective view showing the front, right side, and top of an applicator constructed according to the invention.
Figure 2:
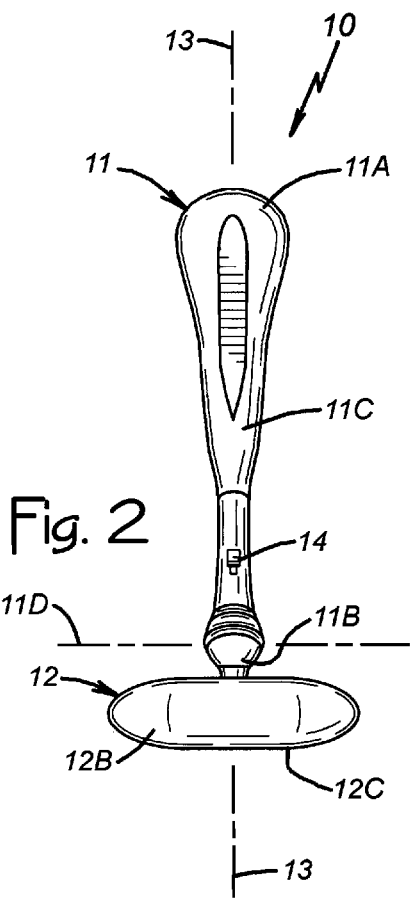
FIG. 2 is a front elevation view of the applicator.
Figure 3:
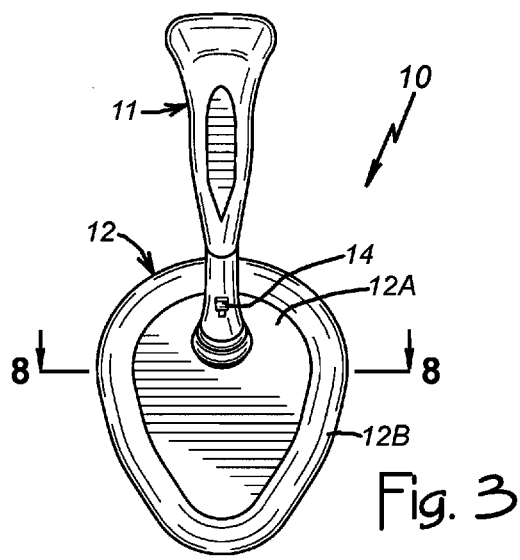
FIG. 3 is a top plan view.

FIGS. 1 through 7 of the drawings show various aspects of an applicator 10 constructed according to the invention. Generally, the applicator 10 includes a handle component 11 and a sponge component 12 (FIGS. 1-6). The handle component 11 is an elongated part (e.g., a plastic part measuring about 5 inches long) that extends along a straight-line axis of elongation 13 (FIG. 2). It has a proximal end portion 11A, a distal end portion 11B, and an intermediate portion 11C (FIGS. 1 and 2) that extends between the proximal and distal end portions. The sponge component 12 mounts removably on the distal end portion 11B.

To use the applicator 10, a caregiver or other user grasps the handle component 11, removes a sponge-sealing cover from the sponge component 12, and mounts the sponge component 12 removably on the distal end portion of the handle component 11. Next, the user proceeds to apply a rash-treating substance that is already on the sponge-component 12 to a rash-affected area, or other area being treated topically, by moving the sponge component 12 across the area being treated. The rash-treating substance was added to the sponge component 12 as part of the manufacturing process. After applying the rash-treating substance, the caregiver slides a slide component 14 (FIGS. 1, 2, 3, and 5) of the handle component 11 distally in order to thereby release the sponge component 12 so that the sponge component 12 can be discarded. Proceeding that way, the rash-treating substance is not transferred to the caregiver's hands.

The sponge component 12 includes a sponge-holding portion 12A (FIGS. 1 and 3) and a sponge portion 12B (FIGS. 1, 2, 3, 4, and 5) that is held by the sponge-holding portion. The sponge-holding portion 12A (e.g., a plastic plate) is glue, bonded, or otherwise suitable attached to the sponge portion 12B in order to hold the sponge portion 12B; the sponge-holding portion 12A functions as means for interfacing (i.e., mounting) the sponge portion 12B of the sponge component 12 to the distal end portion 11B of the handle component 11. Preferably, the distal end portion 11B of the handle component 11 is adapted to pivot about a pivotal axis 11D. The pivotal axis 11D extends perpendicular to the axis of elongation 13, as depicted in FIG. 2. Pivotal motion facilitates use of the applicator 10.

The sponge portion 12B includes a body of material composed of any of various known natural or synthetic materials that form a lightweight, porous, absorbent material for applying the rash-treating substance. The rash-treating substance may be any of various known creams, pastes, ointments and the like that are used to treat rash, and it is added to the sponge portion 12B at the time the sponge component 12 is manufactured. The caregiver applies it by moving a bottom side 12C (FIGS. 1, 2, 4, 5, and 6) of the sponge portion 12B across an area being treated, thereby rubbing the rash-treating substance onto the area being treated.

FIG. 7 shows a sponge-sealing cover 12D diagrammatically as a broken line circumscribing the sponge component 12. The sponge-sealing cover 12D is added during the manufacture of the sponge component 12, after the rash-treating substance is added. The cover 12D may take the form of any of various known thin plastic materials (e.g., transparent plastic sheet material) that provides an airtight seal over the sponge portion 12B. Typically, the caregiver tears or otherwise removes the cover 12D before mounting the sponge component 12 on the handle component 11, although it may be removed after mounting on the handle component 11.

The 5-inch handle dimension mentioned previously gives an idea of component size. The drawings are approximately to scale (except for the diagrammatic view of FIG. 8) so that the size of other components can be estimated by comparing their size to the 5-inch long handle component. Of course, those dimensions may vary significantly without departing from the broader inventive concepts.

Figure 8:
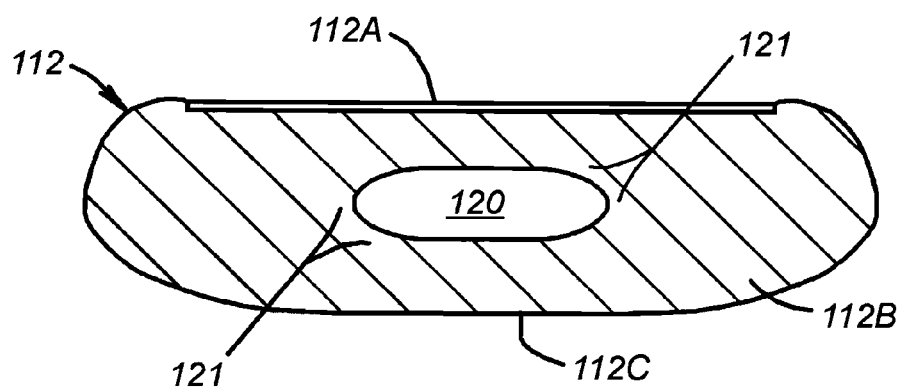
FIG. 8 is an enlarged-in-scale diagrammatic cross-sectional view of the sponge component as viewed in a vertical plane containing a line 8-8 in FIG. 3.

In a second embodiment of the invention, the rash-treating substance is contained within a sealed cavity 120 in the sponge portion 112B (FIG. 8). The second embodiment is generally similar to the applicator 10 except for that feature. For convenience, reference numerals designating parts in FIG. 8 are increased by one hundred over those designating similar, related, or associated parts in FIGS. 1-7. The sponge component 112 of the second embodiment includes a sponge portion 112B beneath a sponge-holding portion 112A; a cavity-defining part 121 of the sponge portion 112B defines the sealed cavity 120, and the sealed cavity 120 contains a quantity of rash-treating substance. To use the second embodiment, the caregiver breaks the seal so that the rash-treating substance flows from the cavity 120 in the cavity-defining part 121 toward the bottom 112C of the sponge portion 112B where it is available to be transferred to the area being treated when the bottom 112C is moved across the area being treated. One such second embodiment is configured so that the action of mounting the sponge component 112 on the handle component 11 pierces or otherwise unseals the cavity-defining part (i.e., it releases the rash-treating substance from the cavity). Stated another way, the sponge portion defines a cavity, the cavity contains the quantity of the rash-treating substance, and the applicator is so adapted that the action of a user mounting the sponge component on the handle component unseals (i.e., releases) the rash-treating substance from the cavity. The applicator is so adapted in the sense that it is configured to function as described above.

Thus, the invention provides an applicator having a handle component and a disposable sponge component that cooperate to facilitate topical application of a rash-treating substance to a baby's bottom without transferring the substance to the caregiver's hands. Based upon the foregoing description and the claims, a person having ordinary skill in the art can readily implement an applicator according to the invention. Although exemplary embodiments have been shown and/or described, a person having ordinary skill in the art may make many changes, modifications, and substitutions without necessarily departing from the spirit and scope of the invention. As for the specific terminology used to describe the exemplary embodiment, it is not intended to limit the invention; each specific term is intended to include all technical equivalents that operate in a similar manner to accomplish a similar purpose or function.

What is claimed is:

1. An applicator for a caregiver to grasp in topically applying a rash-treating substance to a baby's bottom, the applicator comprising:
   a handle component; and
   a sponge component for mounting removably on a distal end portion of the handle component;
   wherein the sponge component has a sponge-holding portion and a sponge portion held by the sponge-holding portion;
   wherein the sponge-holding portion of the sponge component is a plate attached to the sponge portion, said sponge-holding portion functioning as means for interfacing the sponge portion to the distal end portion of the handle component;
   wherein the sponge-holding portion of the sponge component is adapted to be mounted removably on the distal end portion of the handle component;
   wherein the sponge portion of the sponge component includes a quantity of a rash-treating substance;
   wherein the sponge portion defines a cavity;
   wherein the cavity contains the quantity of the rash-treating substance;
   wherein the applicator is so adapted that the action of a user mounting the sponge component on the handle component unseals the rash-treating substance from the cavity;
   wherein the handle component has a length and said length is approximately five inches;
   wherein the handle component extends along a straight-line axis of elongation throughout substantially the entire length of the handle component; and
   wherein the sponge component includes a thickness that is not less than approximately one-half inch.

2. An applicator as recited in claim 1, wherein:
   the sponge portion of the sponge component is pre-moistened with a rash-treating substance; and
   the sponge portion is covered by a sponge-sealing cover that the caregiver removes prior to using the applicator.

3. An applicator as recited in claim 1, wherein the sponge component snaps removably onto the distal end portion of the handle component.

4. An applicator as recited in claim 1, wherein the handle component is an elongated member with an axis of elongation, and the distal end portion of the handle component is pivotable in a plane containing the axis of elongation.

5. An applicator as recited in claim 1, wherein the handle component includes a slide component that enables the caregiver to release the sponge component from the distal end portion of the handle component by sliding the slide component.

* * * * *